United States Patent
Melsky et al.

(10) Patent No.: US 12,336,757 B2
(45) Date of Patent: Jun. 24, 2025

(54) ENDOSCOPICALLY GUIDED ABLATION CATHETERS WITH THERMALLY RESISTANT BALLOONS

(71) Applicant: CardioFocus, Inc., Marlborough, MA (US)

(72) Inventors: Gerald Melsky, Lexington, MA (US); Lincoln Baxter, Centerville, MA (US); Omar Colon, Nashua, NH (US)

(73) Assignee: CardioFocus, Inc., Marlborough, MA (US)

( * ) Notice: Subject to any disclaimer, the term of this patent is extended or adjusted under 35 U.S.C. 154(b) by 658 days.

(21) Appl. No.: 17/590,950

(22) Filed: Feb. 2, 2022

(65) Prior Publication Data
US 2022/0249164 A1 Aug. 11, 2022

Related U.S. Application Data

(60) Provisional application No. 63/146,037, filed on Feb. 5, 2021.

(51) Int. Cl.
*A61L 29/06* (2006.01)
*A61B 18/24* (2006.01)
(Continued)

(52) U.S. Cl.
CPC .............. *A61B 18/24* (2013.01); *A61L 29/06* (2013.01); *A61L 29/085* (2013.01);
(Continued)

(58) Field of Classification Search
CPC .......... A61B 18/24; A61B 2018/00101; A61B 2018/00202; A61B 2018/0022;
(Continued)

(56) References Cited

U.S. PATENT DOCUMENTS

| | | |
|---|---|---|
| 5,499,980 A | 3/1996 | Euteneuer |
| 6,610,035 B2 | 8/2003 | Yang et al. |

(Continued)

FOREIGN PATENT DOCUMENTS

| | | |
|---|---|---|
| EP | 0214721 | 3/1987 |
| EP | 2380603 | 10/2011 |

(Continued)

OTHER PUBLICATIONS

International Search Report and Written Opinion in PCT Application No. PCT/US2022/014864, mailed Jun. 14, 2022 (16 pages).

(Continued)

*Primary Examiner* — Ankit D Tejani
*Assistant Examiner* — Joshua Brendon Solomon
(74) *Attorney, Agent, or Firm* — Leason Ellis LLP

(57) ABSTRACT

An ablation catheter that includes a shaft having a distal end and a balloon coupled to the shaft. The balloon has an inner surface and an opposite outer surface. The inner surface has a proximal region including a proximal balloon end, a main center region, and a distal region including a distal balloon end. The ablation catheter also includes an energy emitter disposed inside the balloon and being configured to move both axially and rotationally within the inside of the balloon. The ablation catheter includes a thermally resistant coating disposed along the inner surface of the balloon within at least the main center region of the inner surface of the balloon. The thermally resistant coating is formed of a material selected from a group consisting of: silicone rubber, polyisoprene, polyurethane.

8 Claims, 2 Drawing Sheets

Figure 1:
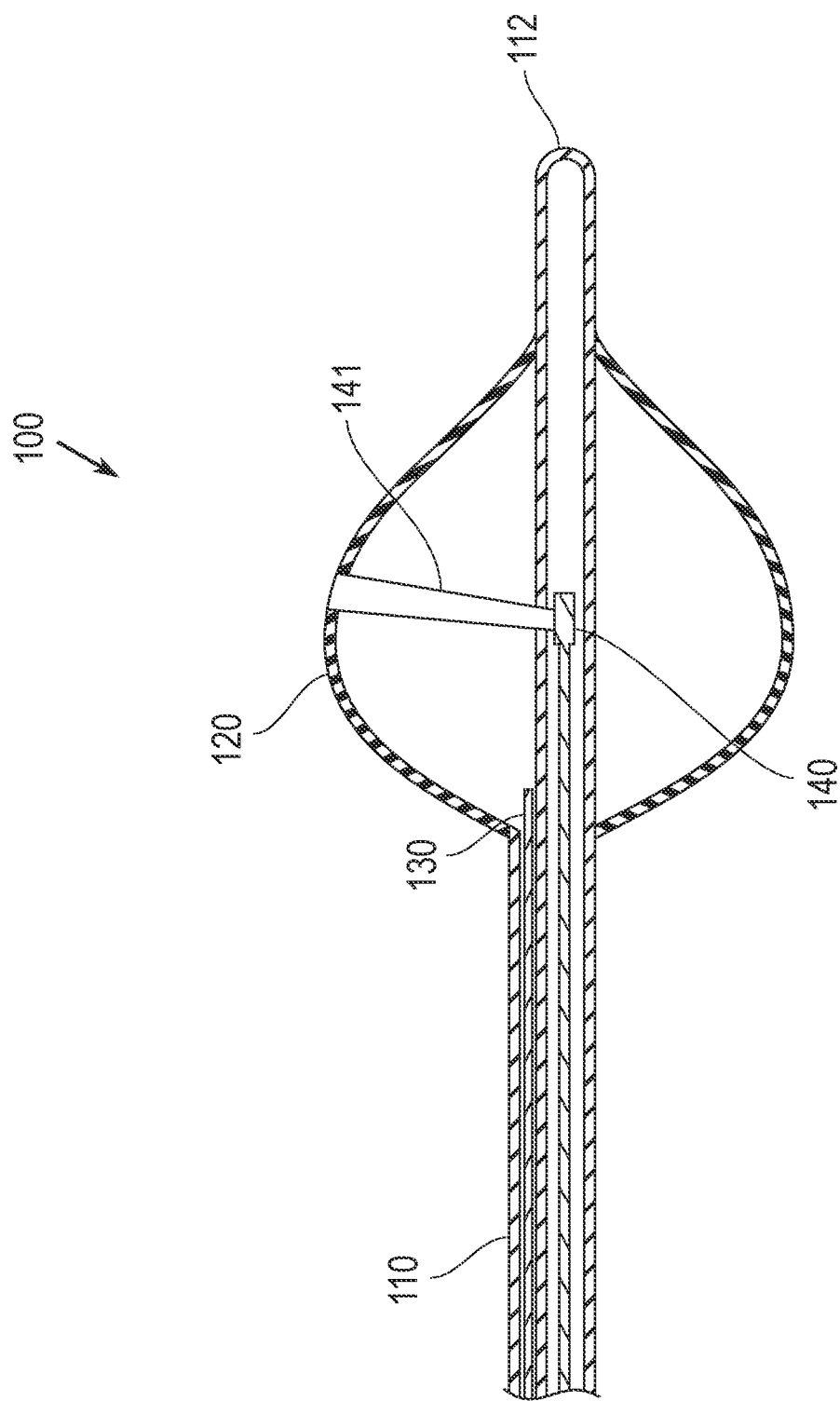

(51) Int. Cl.
*A61L 29/08* (2006.01)
*A61B 18/00* (2006.01)

(52) U.S. Cl.
CPC .............. *A61B 2018/00101* (2013.01); *A61B 2018/00202* (2013.01); *A61B 2018/0022* (2013.01); *A61L 2420/02* (2013.01)

(58) Field of Classification Search
CPC ........... A61B 2018/00386; A61L 29/06; A61L 29/085; A61L 2420/02; C08L 83/04; C08L 75/04
See application file for complete search history.

(56) References Cited

U.S. PATENT DOCUMENTS

| | | | |
|---|---|---|---|
| 6,908,681 B2 | 6/2005 | Terry et al. | |
| 6,923,827 B2 | 8/2005 | Campbell et al. | |
| 6,946,173 B2 | 9/2005 | Lim et al. | |
| 7,892,203 B2 | 2/2011 | Lenker et al. | |
| 7,951,413 B2 | 5/2011 | El-Nounou et al. | |
| 8,267,932 B2 | 9/2012 | Baxter et al. | |
| 9,033,961 B2 | 5/2015 | Melsky et al. | |
| 9,421,066 B2 | 8/2016 | Melsky et al. | |
| D851,245 S | 6/2019 | Baxter et al. | |
| 10,517,669 B2 | 12/2019 | Peled et al. | |
| 10,926,067 B2 | 2/2021 | Melsky et al. | |
| 2002/0146557 A1 | 10/2002 | Claude et al. | |
| 2003/0149468 A1 | 8/2003 | Wallsten | |
| 2004/0073164 A1* | 4/2004 | Boatman | C08G 69/48 604/103.06 |
| 2004/0175558 A1 | 9/2004 | El-nounou et al. | |
| 2005/0222584 A1 | 10/2005 | Kilpatrick et al. | |
| 2010/0049192 A1* | 2/2010 | Holtz | A61N 1/36071 606/41 |
| 2019/0216540 A1* | 7/2019 | Melsky | A61B 18/18 |
| 2019/0343580 A1* | 11/2019 | Nguyen | A61B 18/1492 |
| 2020/0197086 A1 | 6/2020 | Azamian et al. | |
| 2020/0338319 A1 | 10/2020 | Bluemel et al. | |

FOREIGN PATENT DOCUMENTS

| | | |
|---|---|---|
| JP | 2015029562 | 2/2015 |
| WO | 9517920 A1 | 7/1995 |
| WO | 2003022167 A1 | 3/2003 |

OTHER PUBLICATIONS

Extended European Search Report in EP Application No. 22750287.9-1122/4287974, mailed Oct. 14, 2024 (7 pages).

* cited by examiner

ENDOSCOPICALLY GUIDED ABLATION CATHETERS WITH THERMALLY RESISTANT BALLOONS

CROSS REFERENCE RELATED APPLICATION

The present application claims priority to and the benefit of U.S. patent application Ser. No. 63/146,037, filed Feb. 5, 2021, which is hereby incorporated by reference in its entirety.

TECHNICAL FIELD

The present disclosure relates to catheters which are introduced into the human body for the purpose of performing a treatment that involves delivery of energy through a thin membrane. More specifically, it relates to balloon catheters introduced into the left atrium of the heart which deliver laser energy to areas of the left atrium under direct endoscopic visualization for the purpose of treating a medical condition called atrial fibrillation. In yet another aspect, the present disclosure relates to an endoscopically guided ablation catheter with a thermally resistant balloon defined by a thermally resistant coating formed along an inner surface of the balloon.

BACKGROUND

Most commonly, the treatment area is the region near where the pulmonary veins join the left atrium. Such a procedure is called pulmonary vein isolation. To accomplish an effective pulmonary vein isolation, laser energy must be applied to a continuous ring of tissue around the ostium of each pulmonary vein. The goal of the laser energy application is to kill myocytes and generate scar tissue which blocks conduction of electrical signals between the pulmonary veins and the atrial chamber.

Current devices available for endoscopically guided laser balloon ablation for pulmonary vein isolation consist of a multi-lumen catheter with a balloon at the distal end and a handle at the proximal end. An optical fiber in one lumen delivers laser energy through the catheter into the balloon where it is then projected radially toward the balloons surface. In addition to the laser fiber there is a fiber optic endoscope that is inserted through a second lumen of the catheter. The endoscope allows the operator of the catheter to visualize the balloon surface and thereby aim the laser energy to those portions of the balloon surface which contact the atrial tissue it is desired to treat with the laser energy. Such a system is illustrated in FIG. 1 and is described in Melsky et al U.S. Pat. No. 9,421,066B2 and Melsky et al U.S. Pat. No. 9,033,961B2, both of which are hereby expressly incorporated by reference in its entirety.

SUMMARY

According to one embodiment, an ablation catheter is provided and includes a shaft having a distal end and a balloon coupled to the shaft. The balloon has an inner surface and an opposite outer surface. The inner surface has a proximal region including a proximal balloon end, a main center region, and a distal region including a distal balloon end. The ablation catheter also includes an energy emitter disposed inside the balloon and being configured to move both axially and rotationally within the inside of the balloon. The ablation catheter includes a thermally resistant coating disposed along the inner surface of the balloon within at least the main center region of the inner surface of the balloon. The thermally resistant coating is formed of a material selected that can be selected from a group consisting of: silicone rubber, polyisoprene, polyurethane.

The advantage to adding the inner coating is that the inner coating (e.g., silicone rubber) is a material that is much more resistant to high temperatures than the thermoplastic polyurethane that is currently the preferred material for the balloon itself. As a result, the working (active) part of the balloon is protected from the heat generated by the emitted ablation energy.

BRIEF DESCRIPTION OF THE DRAWING FIGURES

Figure 2:
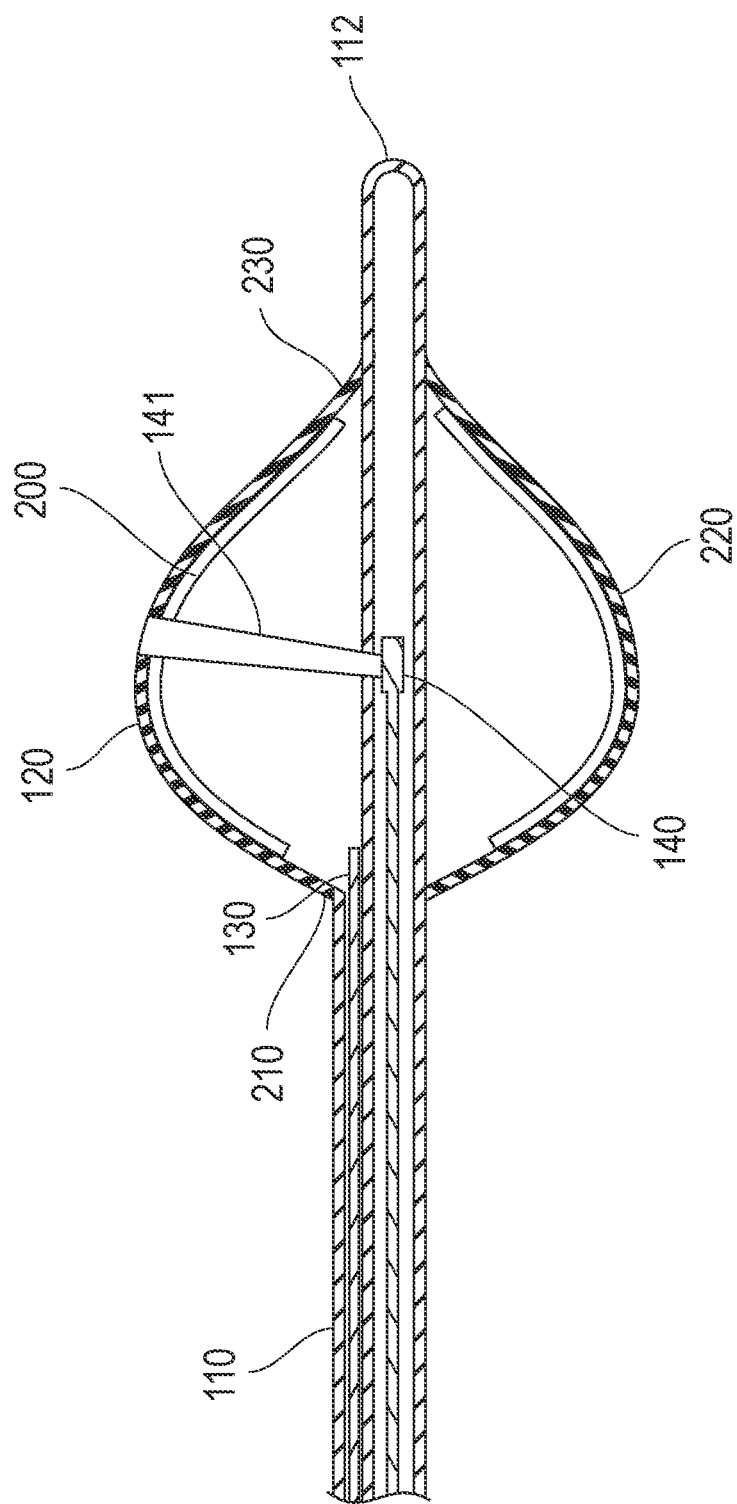

FIG. 1 is a side elevation view of an ablation catheter according to the prior art; and FIG. 2 is a side elevation view of an ablation catheter that includes a thermally resistant coating that covers at least a section of an inner surface of the balloon.

DETAILED DESCRIPTION OF CERTAIN EMBODIMENTS

The present disclosure sets forth an important improvement to balloons described in Melsky et al U.S. Pat. No. 9,421,066B2 and Melsky et al U.S. Pat. No. 9,033,961B2.

The improvement disclosed herein is to add a silicone rubber coating, or a coating of another suitable, thermally resistant material to the inside of the balloon described in Melsky et al U.S. Pat. No. 9,421,066B2 and Melsky et al U.S. Pat. No. 9,033,961B2 or other similar devices. In other words, the coating described herein can be included with other types of ablation balloons and not limited to those balloons described in Melsky.

FIG. 1 shows one exemplary ablation catheter (ablation system) 100 that is similar to or identical to those described in the Melsky patents identified above, as well as, U.S. Pat. No. 10,926,067, which is hereby expressly incorporated by reference in its entirety.

In general, the ablation catheter 100 is of a type that emits ablation energy sufficient to cause formation of an ablation at a tissue target site.

The ablation catheter 100 further preferably includes an aiming light source (not shown) and an illumination light source (not shown). The ablation catheter 100 also includes a processor designed to accept input and output data from the connected instruments, a display (not shown), and a controller (not shown) and process that data into visual information. The ablation catheter 100 includes an elongated shaft 110 that has a closed distal end 112. Within the hollow shaft 110, there are typically a plurality of lumens that provide fluid transport. An inflatable balloon 120 (e.g., a compliant balloon) surrounds a portion of the shaft 110 near the distal end 112 and is in fluid communication with an inflation lumen that permits inflation fluid to be delivered and removed from the balloon 120 for inflation and deflation of the balloon 120.

The ablation catheter 100 also includes an endoscope 130 that has the capability of capturing both live images and recording still images. The illumination light can be used to provide operating light to the treatment site. The illumination light is of a frequency that allows the user to differentiate between different tissues present at the operating site. The aiming light source is used to visualize the location where energy will be delivered by the ablation catheter 100 to tissue. It is envisioned that the aiming light will be of a wavelength that can be recorded by an image capture device and visible on a display.

In one embodiment, the ablation catheter 100 includes an elongated body with a central lumen tubing and the compliant balloon 120 is inflatable via one or more ports in the central tubing. The central tubing can also house an energy emitter 140 that is capable of both axial movement and rotation within a lumen formed in the elongate body as described in detail in the above-identified patents. As depicted, the energy emitter 140 is typically a side firing energy emitter in that the emitted energy (e.g., laser energy) is emitted radially outward from the side of the central tubing (and the balloon 120). As shown, the emitted energy passes through the balloon 120 before reaching the target tissue. In the figures, the emitted energy is shown at 141.

The endoscope 130 is located proximal to the energy emitter 140 and is forward facing to capture the image of the balloon and the emitted energy location as well as the aiming beam illumination, etc.

Inner Coating within Balloon

One exemplary embodiment is shown schematically in FIG. 2 in which an inner coating, generally shown at 200 has been added to the inner surface of the balloon 120. As described herein, in one embodiment, the inner coating 200 is formed of a silicone rubber. The advantage to adding the inner coating 200 is that inner coating (e.g., silicone rubber) is a material that is much more resistant to high temperatures than the thermoplastic polyurethane that is currently the preferred material for the balloon 120. When using the device described in Melsky et al U.S. Pat. No. 9,421,066B2 and Melsky et al U.S. Pat. No. 9,033,961B2 atrial tissue is heated by laser energy to a temperature high enough to kill myocytes and cause the atrial tissue to eventually heal as non-electrically conducting scar tissue. The threshold temperature for accomplishing this is generally considered to be 50° C. However, under some circumstances, the balloon material may be locally heated to a temperature approaching or exceeding the Vicat softening point of the preferred thermoplastic polyurethane material used for the balloon which is 82° C. One such circumstance is if laser energy is delivered into a region of stagnant blood that is in contact with tissue. Blood absorbs the 980 nm laser light used for tissue ablation very readily and can reach localized temperatures of 100° C. or greater. While this temperature is high enough when combined with the mechanical stress placed on the balloon as a consequence of it being inflated, to cause mechanical failure of the balloon material, such an increased temperature takes place only over a very small area of the balloon 120. Consequently, any mechanical failure of the balloon material manifests as simply the creation of a microscopic pinhole in the balloon material. Formation of such a pinhole results in a very small leak of the liquid filling the balloon and is generally of only minor consequence. However, if it is necessary to deflate the balloon in order to reposition the balloon within the atrium, the negative pressure created inside the balloon during deflation my, on occasion, draw blood into the balloon. In such an instance, the catheter must be replaced. This is obviously undesirable and costly.

As shown in FIG. 2, the inner coating 200 covers at least a target inner surface (working area) of the balloon 120. For example, the inner coating 200 in one embodiment does not cover the entire inner surface of the balloon 120. For example, the balloon 200 can be thought of as including a proximal region 210, a main center region 220, and a distal region 230. The main center region 220 is located between the proximal region 210 and the distal region 230. This main center region 220 defines the area in which the energy from the energy emitter 140 is projected and passes through the balloon 120. Since balloon protection is only required in the region in which the energy is actively transmitted, the inner coating 200 only needs to be present in this region 220. Thus, the inner coating 200 can be absent from both the proximal region 210 and the distal region 230 since energy is not emitted in these regions.

However, in another embodiment, the inner coating 200 is applied to substantially the entire inner surface of the balloon 120 (i.e., at least 90% of the inner surface area of the balloon).

In one embodiment, between 50% and 90% of the surface area of the inner surface of the balloon 120 is coated with the coating 200. In another embodiment, between 75% and 90% of the surface area of the inner surface of the balloon 120 is coated with the coating 200.

From the above description of the thermal environment in which the balloon is used it is apparent that a more thermally robust material is desirable. However, thermal resistance is not the only requirement for the balloon material. In addition, the balloon material must be transparent to the 980 nm laser light and to visible light. Transparency to visible light is necessary to allow the balloon to be positioned under endoscopic guidance as described in Melsky et al U.S. Pat. No. 9,421,066B2 and Melsky et al U.S. Pat. No. 9,033, 961B2. Also, the balloon must be compliant in order that it may conform to the anatomy of the left atrium, particularly the anatomy of the pulmonary vein ostia which are the regions were ablation is usually performed to treat atrial fibrillation. The balloon must also be of a lubricious nature or at least lubricious enough to be easily introduced into and removed from the left atrium utilizing a guide catheter or deflectable sheath such as that described in Baxter et al U.S. Pat. No. 8,267,932B2, which is hereby incorporated by reference in its entirety.

A polyurethane balloon coated internally with silicone rubber (coating 200) satisfies all of the requirements mentioned above. Silicone rubber is optically transparent as well as transparent to 980 nm laser light. Silicone rubber is thermally resistant. Silicone rubber has high surface friction so a balloon coated on the outside with silicone rubber would fail to meet the requirement that the balloon be of a lubricious nature or at least lubricious enough to be easily introduced into and removed from the left atrium utilizing a guide catheter or deflectable sheath. However, coating the inside of the balloon with silicone rubber or suitable material satisfies the lubricity requirement since the polyurethane exterior of the balloon material contacts the lumen of the guide catheter or sheath and not the high friction silicone rubber coated interior.

While some degree of compliance is desirable, a very high degree of compliance is a disadvantage. The reason why too much compliance is a disadvantage is two-fold. First, a balloon made from too highly compliant a material tends to always inflate to a spherical shape. It has been determined that optimal positioning of a balloon ablation catheter is most easily achieved when the balloon has a generally tapered shape as illustrated in Baxter and Melsky USD851245S1. The second reason that too much compliance is a disadvantage is that a very compliant balloon can be too easily deformed by forces applied to the shaft of the catheter to which the balloon is attached. An endoscopically guided ablation catheter works best when the shaft of the catheter that passes through the central axis of the balloon remains relatively centered in the balloon. With the shaft centered an optimal endoscopic view of balloon contact with the vein is obtained. If the shaft becomes significantly off center, the endoscope that is attached to the central shaft may end up in a position where only part of the vein contact with the balloon is visualized. In an extreme case, the shaft endoscope may be pushed onto contact with the pulmonary vein wall, entirely obscuring the view from the endoscope.

Because a specific degree of compliance is important for optimal functioning of an endoscopically guided balloon ablation catheter, it is desirable that any modifications to the balloon for the purpose of increasing the balloon's resistance to thermal pinholes would not change the mechanical properties of a balloon that has demonstrated acceptable mechanical properties. In the case of the current invention 80 Shore A durometer polyurethane has demonstrated acceptable mechanical properties. Coating the inner surface of an 80 Shore A durometer polyurethane balloon with a layer of silicone rubber having a stress at 100% strain of 65 PSI or lower will result in a final balloon configuration with mechanical properties that are essentially no different than the polyurethane balloon without the silicone coating. This is because the silicone with stated stress vs strain characteristic is significantly more elastic than the urethane. Therefore, the silicone coating, while improving the balloon's resistance to pinholes will not cause the compliance of the coated urethane balloon to be noticeably different form that of the uncoated balloon.

EXAMPLES

In one embodiment, the coating is formed of a material that is selected from the group consisting of: silicone rubber, polyisoprene, polyurethane. In particular, one preferred groups of materials are either thermoset materials or materials with a vicat softening point above 150 degrees Celsius. Silicone rubber is particularly of interest due to its clarity, high temperature resistance and known biocompatibility.

In one embodiment, the coating has a thickness of between 0.0005" (inches) to 0.004" (inches). For example, the coating can have a thickness of between 0.001" (inches) to 0.002" (inches).

In one embodiment, the coating has a coating material hardness of between 25 Shore A to 80 Shore A. For example, the coating can have a coating material hardness of 50 Shore A.

In one embodiment, the viscosity of the coating material before curing is between 1 centipoise to 40 centipoise and more particularly, can be between 10 to 20 centipoise.

Methods of Producing a Coated Balloon

Manufacturing methods for the coated balloon are familiar to those skilled in the art. Thin polymer (silicone) coatings can be applied by dipping, spraying, brush application or rotational molding.

Since it is preferred to coat the internal surface of the balloon, a rotational molding type of application method is the preferred method. In normal rotational molding, material is introduced into a mold cavity while in the liquid state and the mold is rotated about two or more axes of rotation simultaneously in order to evenly distribute the liquid state material evenly over the surface of the mold and maintain the even distribution of the material while the material solidifies. Once solidified, rotation is stopped and the mold is separated along a parting line in order to remove the molded material which presents as a shell of material mimicking the shape of the mold.

In order to produce polyurethane balloons coated internally with silicone rubber, the polyurethane balloon itself acts as the mold in one exemplary method of forming the coating. A mixture of prepolymer, crosslinking catalyst and optionally, a volatile solvent used to adjust the mixtures viscosity are introduced into the balloon. The balloon is then rotated or alternatively oscillated about two or more axes simultaneously to distribute the mixture. Rotation and/or oscillation continues until the mixture cures into the solid, silicone rubber state. Alternatively, heat may be applied to the balloon either externally or by introducing a flow of heated air through the balloons interior in order to speed the curing of the material into silicone rubber. One the mixture is filly cured the coated balloon is complete.

In one embodiment, the viscosity of the coating material before the curing step is between 1 centipoise to 40 centipoise. For example, the viscosity of the coating material before curing is between 10 to 20 centipoise.

It may be desirable to enhance the adhesion of the silicone rubber to the polyurethane balloon by coating the inner surface of the balloon with a primer. Such adhesion enhancing primers are well known to those skilled in the art of silicone rubber coating. The primer may be applied in a manner similar to the final application of the silicone rubber prepolymer mixture. In the instance of the primer, curing does not take place but a volatile solvent must be allowed to evaporate, leaving the primer behind on the inner surface of the urethane balloon. For some primer chemistries, the primer is most effective if it first hydrolyzed. Solvent evaporation is facilitated by a flow of heated air similar to that used to enhance curing of the silicone rubber. Hydrolization is facilitated by introducing a flow of both heated and humidified air through the balloon.

As shown in FIG. 2, the coating is applied to the inner surface (working area) of the balloon that is subjected to the energy emitted by the movable energy emitter (e.g., a fiber optic) that is located inside of the balloon. The coating can cover the entire or substantially the entire inner surface of the balloon or can cover less, such as being absent at the immediate ends of the balloon, as discussed hereinbefore.

As mentioned previously, each of the patents and U.S. patent application publications that are listed herein is expressly incorporated by reference in its entirety.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not precludes the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

What is claimed is:

1. A method of treating an inner surface of a balloon of an ablation catheter to increase thermal resistivity of the balloon comprising the steps of:
    positioning the balloon such that the balloon itself acts as a mold;
    preparing a mixture of prepolymer, crosslinking catalyst and optionally, a volatile solvent used to adjust a viscosity of the mixture;
    introducing the mixture into an inside of the balloon;
    rotating or oscillating the balloon about two or more axes simultaneously to distribute the mixture within the inside of the balloon; and
    curing the mixture into a solid polymer coating that covers at least one section of the inner surface of the balloon, the solid polymer coating being more resistant to higher temperatures compared to a material that forms the balloon.

2. The method of claim 1, further comprising the step of:
    applying heat to the balloon either externally or by introducing a flow of heated air through an interior of the balloon in order to speed curing of the mixture into the solid polymer coating.

3. The method of claim 1, further including the step of:
    coating the inner surface of the balloon with a primer.

4. The method of claim 1, wherein the balloon material comprises a thermoplastic polyurethane material and the solid polymer coating comprises a silicone rubber material.

5. The method of claim 1, wherein a viscosity of the mixture prior to curing is between 1 centipoise to 40 centipoise.

6. The method of claim 5, wherein the viscosity of the mixture prior to curing is between 10 to 20 centipoise.

7. The method of claim 1, wherein the at least one section comprises a main center region of the balloon with an adjacent proximal region of the balloon being free of the solid polymer coating and an adjacent distal region of the balloon being free of the solid polymer coating.

8. The method of claim 7, wherein the main center region comprises an area of the balloon through which emitted energy passes.

* * * * *